(12) United States Patent
Murata et al.

(10) Patent No.: US 6,524,556 B2
(45) Date of Patent: *Feb. 25, 2003

(54) AEROSOL COMPOSITIONS

(75) Inventors: Saburo Murata, Hyogo (JP); Fumio Shiomojo, Hyogo (JP); Yuji Tokunaga, Hyogo (JP); Takehisa Hata, Hyogo (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/994,702

(22) Filed: Nov. 28, 2001

(65) Prior Publication Data

US 2002/0061906 A1 May 23, 2002

Related U.S. Application Data

(63) Continuation of application No. 09/029,863, filed on Apr. 22, 1998, now Pat. No. 6,361,760
(60) Provisional application No. PCT/JP96/02670, filed on Sep. 18, 1996, now Pat. No. 6,361,760.

(30) Foreign Application Priority Data

Sep. 19, 1995 (JP) ............................................... 7-239342

(51) Int. Cl.⁷ ..................... A61K 9/12; C07D 491/02; C07D 31/436
(52) U.S. Cl. .............................. 424/45; 424/67; 546/89; 546/79; 514/277; 514/359; 514/451
(58) Field of Search ................. 514/277, 359, 514/451, 449, 430, 354; 424/45, 67; 546/89, 79

(56) References Cited

U.S. PATENT DOCUMENTS

| 4,916,138 | A |   | 4/1990  | Ueda et al. |
| 5,215,995 | A |   | 6/1993  | Honbo et al. |
| 5,368,865 | A |   | 11/1994 | Asakura et al. |
| 5,601,844 | A |   | 2/1997  | Kagayama et al. |
| 5,635,161 | A |   | 6/1997  | Adjei et al. |
| 5,681,501 | A |   | 10/1997 | Minor |
| 5,770,607 | A |   | 6/1998  | Honbo et al. |
| 5,817,333 | A | * | 10/1998 | Kagayama et al. ......... 424/450 |
| 5,939,427 | A |   | 8/1999  | Kagayama et al. |
| 5,955,469 | A |   | 9/1999  | Asakura et al. |
| 6,284,226 | B1 | * | 9/2001 | Ito et al. ...................... 424/45 |
| 6,316,473 | B1 |   | 11/2001 | Shimojo et al. |

FOREIGN PATENT DOCUMENTS

| EP | 0 184 162    | 6/1986 |
| WO | WO 92/08474  | 5/1992 |
| WO | WO 96/00058  | 1/1996 |

* cited by examiner

*Primary Examiner*—Alan L. Rotman
*Assistant Examiner*—Rita Desai
(74) *Attorney, Agent, or Firm*—Oblon, Spivak, McClelland, Maier & Neustadt, P.C.

(57) ABSTRACT

The use of a medium-chain fatty acid triglyceride as the dispersant in the preparation of a medicinal aerosol composition comprising tricyclic compound (I) dispersed in a liquefied hydrofluoroalkane propellant is described.

When a liquefied hydrofluoroalkane is added to a kneaded premix of the tricyclic compound (I) and a medium-chain fatty acid triglyceride, the active ingredient is evenly dispersed in the liquefied hydrofluoroalkane.

Therefore, by distributing a dispenser first with the kneaded premix and, then, with a liquefied hydrofluoroalkane under cooling or elevated pressure, there can be provided a medicinal aerosol composition an improved uniformity of content of the active ingredient.

13 Claims, No Drawings

AEROSOL COMPOSITIONS

This application is a Continuation of U.S. application Ser. No. 09/029,863, filed on Apr. 22, 1998, now U.S. Pat. No. 6,361,760, which is a 371 or PCT/JP96/02670, filed Sep. 18, 1996.

TECHNICAL FIELD

This invention relates to a medicinal aerosol composition and a process for the preparation of the same and, as such, finds application in the field of medicine.

BACKGROUND ART

A tricyclic compound (I) and a pharmaceutically acceptable salt thereof used in the present invention have been known to possess excellent pharmacological activities such as an immunosuppressive activity and an antimicrobial activity, thereby being useful for treating and/or preventing rejection by organ-transplantation or tissue-transplantation, graft-versus-host diseases, various autoimmune diseases and infectious diseases (for example, see EP-A-0184162 and WO 89/05304).

Particularly, compounds referred to as FR900506(=FK506), FR900520, FR900523 and FR900525 which belong to the tricyclic compound (I) are produced from genus Streptomyces, in particular, *Streptomyces tsukubaensis* No. 9993 (Depositary Authority: 1–3, Higashi 1 chome, Yatabe-machi, Tsukuba-gun, Ibaraki-ken, Japan, Fermentation Research Institute Agency of Industrial Science and Technology, Ministry of International Trade and Industry; Date of the Deposit: Oct. 5, 1984; Accession Number: FERM BP-927) or *Streptomyces hygroscopicus* Subsp. *vakushimaensis* No. 7238 (Depositary Authority: 1–3, Higashi 1 chome, Yatabe-machi, Tsukuba-gun, Ibaraki-ken, Japan, Fermentation Research Institute Agency of Industrial Science and Technology, Ministry of International Trade and Industry; Date of the Deposit: Jan. 12, 1985; Accession Number: FERM BP-928). Such situations are shown in EP-A-0184162.

Among those tricyclic compound (I), FK506 represented by the following structural formula is a typical compound.

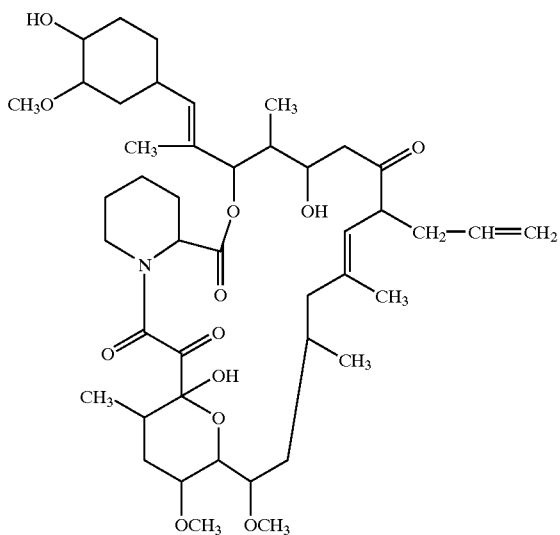

Generic name: Tacrolimus
Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

On the other hand, a medicinal aerosol is a drug delivery system adapted to deliver a medicinally active substance in a finely divided form along with inspired air into the recipient's airway for the treatment of attacks of bronchial asthma, for instance, and is in broad use in the field of medicine.

The conventional medicinal aerosol utilizes one or more kinds of liquefied chlorofluorocarbons (hereinafter referred to collectively as CFC) as the propellant and is available in a system such that a finely divided medicinally active substance has been dispersed in CFC with the aid of a suitable dispersant.

For example, aerosol of the tricyclic compound (I) comprising such CFC were already suggested in WO 90/14826.

However, CFC is associated with the on-going destruction of the ozone layer of the atmosphere and a worldwide total ban on its use is foreseen within this century. Under the circumstances, the use of liquefied hydrofluoroalkanes (hereinafter sometimes referred to collectively as HFA) is being contemplated as substitute propellants for aerosols. However, despite their advantage of being lenient to the ozonosphere in comparison with CFC, HFA has the disadvantage that because of the total insolubility of the conventional dispersants (e.g. soybean lecithin) therein, medicinally active substances cannot be successfully dispersed in HFA.

To overcome the above disadvantage, an aerosol system providing for a uniform dispersion of a medicinally active substance has been proposed which comprises HFA and, as a dispersant, a polymer containing an HFA-soluble amide or carboxylic ester as a recurrent unit (such as polyvinylpyrrolidone, polyvinyl acetate, acrylic acid-methacrylic ester copolymer) (WO 93/05765).

The polymer used in the above aerosol system is a solid substance, with the result that when a premix of the polymer with the active substance is to be dispersed in the propellant, there occurs a segregation of the active ingredient. Therefore, it is common practice to feed the active substance and the polymer respectively to a cooling agitation tank or a pressure tank, then adding HFA under cooling or elevated pressure with stirring to disperse the active substance in the HFA, and distributing the dispersion into dispensing containers. However, this procedure is not only complicated but also has the disadvantage that because the proportion of the active ingredient is quite small, a uniformity of its content for each dispenser can hardly be insured in the stage of portion-wise distribution of the propellant dispersing the active ingredient.

SUMMARY OF THE INVENTION

This inventors of this invention did much research for overcoming the above-mentioned disadvantages and discovered that when a medium-chain fatty acid triglyceride is used as the dispersant in the manufacture of a medicinal aerosol, the tricyclic compound (I) can be uniformly dispersed in HFA by kneading the tricyclic compound (I) with the medium-chain fatty acid triglyceride in the first place, distributing the kneaded mass into aerosol dispensers, and filling the respective dispensers with HFA under cooling or elevated pressure and that, as a result, not only the aerosol preparation process is simplified but also the final aerosol has a minimal dispenser-to-dispenser variation in content of the active ingredient. They accordingly have perfected this invention.

DETAILED DESCRIPTION OF THE INVENTION

The aerosol composition of this invention comprises a tricyclic compound (I) or a pharmaceutically acceptable salt thereof mentioned below, a liquefied hydrofluoroalkane, and a medium-chain fatty acid triglyceride.

The tricyclic compound (I) used in the present invention is represented by the following formula:

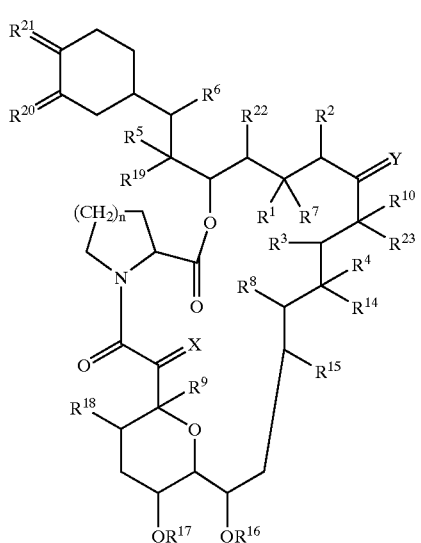

(I)

wherein each of adjacent pairs of $R^1$ and $R^2$, $R^3$ and $R^4$ or $R^5$ and $R^6$ independently
(a) is two adjacent hydrogen atoms, or
(b) may form another bond formed between the carbon atoms to which they are attached,
and further, $R^2$ may be an alkyl group;
$R^7$ is a hydrogen atom, a hydroxy group, a protected hydroxy group or an alkoxy group, or an oxo group together with $R^1$;
each of $R^8$ and $R^9$ is independently a hydrogen atom or a hydroxy group;
$R^{10}$ is a hydrogen atom, an alkyl group, an alkyl group substituted by one or more hydroxy groups, an alkenyl group, an alkenyl group substituted by one or more hydroxy groups or an alkyl group substituted by an oxo group;
X is an oxo group, (a hydrogen atom and a hydroxy group), (a hydrogen atom and a hydrogen atom), or a group represented by the formula —CH$_2$O—;
Y is an oxo group, (a hydrogen atom and a hydroxy group), (a hydrogen atom and a hydrogen atom), or a group represented by the formula N—NR$^{11}$R$^{12}$ or N—OR$^{13}$;
each of $R^{11}$ and $R^{12}$ is independently a hydrogen atom, an alkyl group, an aryl group or a tosyl group;
each of $R^{13}$, $R^{14}$, $R^{15}$, $R^{16}$, $R^{17}$, $R^{18}$, $R^{19}$, $R^{22}$ and $R^{23}$ is independently a hydrogen atom or an alkyl group;
each of $R^{20}$ and $R^{21}$ is independently an oxo group or ($R^{20}$a and a hydrogen atom) or ($R^{21}$a and a hydrogen atom) in which each of $R^{20}$a and $R^{21}$a is independently a hydroxy group, an alkoxy group or a group represented by the formula —OCH$_2$OCH$_2$CH$_2$OCH$_3$, or $R^{21}$a is a protected hydroxy group, or $R^{20}$a and $R^{21}$a may together represent an oxygen atom in an epoxide ring;
n is an integer of 1, 2 or 3; and
in addition to the above definitions, Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkyl substituted by one or more hydroxy groups, an alkoxy, a benzyl and a group of the formula —CH$_2$Se(C$_6$H$_5$).

Hereinafter, various terms which are included in the scope of the present invention will be defined:

Each definition in the formula (I) will be detailed as follows.

The term "lower" means, unless otherwise indicated, a group having 1 to 6 carbon atoms. Preferable examples of the "alkyl groups" include a straight or branched chain aliphatic hydrocarbon residue, for example, a lower alkyl group such as methyl, ethyl, propyl, isopropyl, butyl, isobutyl, pentyl, neopentyl and hexyl. Preferable examples of the "alkenyl groups" include a straight or branched chain aliphatic hydrocarbon residue having one double-bond, for example, a lower alkenyl group such as vinyl, propenyl (e.g., allyl group), butenyl, methylpropenyl, pentenyl and hexenyl. Preferable examples of the "aryl groups" include phenyl, tolyl, xylyl, cumenyl, mesityl and naphthyl.

Preferable protective groups in the "protected hydroxy groups" are 1-(lower alkylthio) (lower)alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably $C_{1-4}$ alkylthiomethyl group, most preferably methylthiomethyl group; trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyl-diarylsilyl (e.g., methyldiphenylsilyl, ethyldiphenylsilyl, propyldiphenylsilyl, tert-butyldiphenylsilyl, etc.), more preferably tri($C_{1-4}$)alkylsilyl group and $C_{1-4}$ alkyldiphenylsilyl group, most preferably tert-butyldimethylsilyl group and tert-butyldiphenylsilyl group; or an acyl group such as an aliphatic, aromatic acyl group or an aliphatic acyl group substituted by an aromatic group, which are derived from a carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.; a cyclo(lower)alkoxy(lower)alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri-(lower)alkylsilyl (lower)alkoxycarbonyl (lower) alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include ar(lower)alkanoyl group optionally having one or more suitable substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are $C_{1-4}$ alkanoyl group optionally having carboxy, cyclo($C_{5-6}$)alkoxy($C_{1-4}$)alkanoyl group having two ($C_{1-4}$) alkyls at the cycloalkyl moiety, camphorsulfonyl group, carboxy-($C_{1-4}$)alkylcarbamoyl group, tri($C_{1-4}$)alkylsilyl($C_{1-4}$)-alkoxycarbonyl($C_{1-4}$)alkylcarbamoyl group, benzoyl group optionally having one or two nitro groups, benzenesulfonyl group having halogen or phenyl ($C_{1-4}$)alkanoyl group having $C_{1-4}$ alkoxy and trihalo($C_{1-4}$) alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "5- or 6-membered nitrogen, sulfur and/or oxygen containing heterocyclic ring" include a pyrrolyl group and a tetrahydrofuryl group.

The pharmaceutically acceptable salt of the tricyclic compound (I) includes conventional non-toxic and pharmaceutically acceptable salt such as the salt with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the tricyclic compound (I), it is to be understood that there may be conformers and one or more stereoisomers such as optical and geometrical isomers due to asymmetric carbon atom(s) and double bond(s), and such conformers and isomers are also included within the scope of the present invention.

The tricyclic compound of the formula (I) and its salt can be in the form of a solvate, which is included within the scope of the present invention. The solvate preferably include a hydrate and an ethanolate.

FK506 is the most preferable compound belonging to the tricyclic compound (I). Other preferable compounds are listed hereinbelow.

1,14-Dihydroxy-12-[2-(4-hydroxy-3-methoxycyclohexyl)-1-methylvinyl]-23,25-dimethoxy-13,19,17,21,27-pentamethyl-11,28-dioxa-4-azatricyclo[22.3.1.0$^{4,9}$] octacos-18-ene-2,3,10,16-tetraone, 12-[2-(4-acetoxy-3-methoxycyclohexyl)-1-methylvinyl]-17-allyl-1,14-dihydroxy-23,25-dimethoxy-13,19,21,27-tetramethyl-11,28-dioxa-4-azatricyclo[22.3.1.0$^{4,9}$] octacos-18-ene-2,3,10,16-tetraone, 17-allyl-1,14-dihydroxy-23,25-dimethoxy-13,19,21,27-tetramethyl-12-[2-[4-(3,5-dinitrobenzoyloxy)-3-methoxycyclohexyl]-1-methylvinyl]-11,28-dioxa-4-azatricyclo[22.3.1.0$^{4,9}$]-octacos-18-ene-2,3,10,16-tetraone, 17-allyl-12-[2-[4-[(−)-2-trifluoromethyl-2-methoxy-2-phenylacetoxy]-3-methoxycyclohexyl]-1-methylvinyl]-1, 14-dihydroxy-23,25-dimethoxy-13,19,21,27-tetramethyl-11,28-dioxa-4-azatricyclo[22.3.1.0$^{4,9}$octacos-18-ene-2,3, 10,16-tetraone.

17-ethyl-1,14-dihydroxy-12-[(2-(4-hydroxy-3-methoxycyclohexyl)-1-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (FR900520), and 17-ethyl-1,14,20-trihydroxy-12-[2-(3,4-dihydroxycyclohexyl)-1-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone.

The liquefied hydrofluoroalkane that can be used as the propellant in the medicinal aerosol composition of this invention includes but is not limited to 1,1,1,2-tetrafluoroethane ($CH_2FCF_3$, hereinafter HFA-134a) and 1,1,1,2,3,3,3-heptafluoropropane ($CF_3CHCF_3$, hereinafter HFA-227) and these liquefied hydrofluoroalkanes can be used either alone or in combination.

The medium-chain fatty acid triglyceride (MCT) for use as the dispersant for the active ingredient in the aerosol composition of this invention is predominantly composed of the triglycerides of saturated fatty acids [$CH_3(CH_2)_n COOH$, n=4–10], and such commercial products as Miglyol (the trademark of Dynamit Novel) 812, Panacete (the trademark of NOF Corporation) 810, Coconard (the trademark of Kao Corporation), Myritol (the trademark of Hankel-Hakusui) GM, ODO (the trademark of The Nisshin Oil Mills, Ltd.), etc. can be utilized. The above MCT can be used either alone or in combination.

The formulating amount of said medium-chain fatty acid triglyceride is dependent on the type and quantity of the active ingredient but may range generally from 0.05 to 5 w/v % and preferably from 0.1 to 2 w/v %.

The above-mentioned tricyclic compound (I) or a pharmaceutically acceptable salt thereof used in the aerosol composition of the present invention is preferably in the form of fine particles. And in such case, it may be pulverized beforehand to a particle size of about 0.5–5 $\mu$m, more preferably 1–3 $\mu$m, by a conventional method, such as using jet mill. The amount of the tricyclic compound (I) or a pharmaceutically acceptable salt thereof contained in the present aerosol composition is the therapeutically effective one, and varies from and depends on the type of the aerosol composition and the age and condition of each indimisual patient to be treated. However, it is generally 0.001–10 w/v % and preferably 0.005–5 w/v %.

Furthermore, the aerosol composition of this invention may further contain the conventional additives such as dispersant(s) (e.g., polyvinylpyrrolidone, polyvinyl alcohol, sorbitan fatty acid ester, polyoxyethylene-sorbitan fatty acid ester (e.g. Tween 20, Span 85, etc.), fatty acid ester, polyethylene glycol-fatty acid ester, polyoxyethylene alkyl ether, sucrose ester, lecithin, HCO-60 (polyoxyethylenehydrogenated castor oil), oleic acid, isopropyl myristate, etc.), in a proportion of 0.0001–0.05 w/v % and/or solubilizer(s) for the tricyclic compound (I) or a pharmaceutically acceptable salt thereof (e.g., ethanol, glycerin, polyethylene glycol, propylene glycol, etc.), in a proportion of 1–20 w/v %.

The process for the preparation of the aerosol composition according to this invention is characterized by kneading the tricyclic compound (I) or a pharmaceutically acceptable salt thereof and a medium-chain fatty acid triglyceride together, distributing the kneaded mass into dispensers, and filling the respective dispensers with a liquefied hydrofluoroalkane under cooling or elevated pressure.

The more details of the process for preparation of the aerosol composition of the present invention are exemplified as follows.

First, the finely divided tricyclic compound (I) or a pharmaceutically acceptable salt thereof is kneaded with said medium-chain fatty acid triglyceride and optional additives, such as polyvinylpyrrolidone or the like, and the kneaded mass is distributed into dispensing containers (usually aluminum cans). Then, each resulting dispenser is filled with the liquefied hydrofluoroalkane precooled to −20° C. to disperse the active ingredient in the hydrofluoroalkane. The dispenser is then fitted with a valve to provide a finished product.

As an alternative, after distributing the above kneaded mass into dispensing containers, each resulting dispenser may be fitted with a valve and, then, filled with said liquefied hydrofluoroalkane under an elevated pressure of 20–30 atmospheres at ordinary temperature.

The ejection amount of the medicinal aerosol of this invention is 25–150 µl per valve actuation. Depending on the amount of the active substance, 1–3 valve actuations are made per dose and 1–5 doses are administered a day.

EFFECT OF THE INVENTION (1) The tricyclic compound (I) or its salt is insoluble or indispersible in liquefied hydrofluoroalkanes, even if conventional dispersants, such as soya lecithin, are admixed with.

However, by the addition of medium-chain fatty acid triglyceride (MCT), rot. only the improvement of dispersing condition of the tricyclic compound (I) but also the dramatic enhancement of the solubility of the tricyclic compound (I) in liquefied hydrofluoroalkanes were achieved.

As shown in Table 1, the solubility of FK506, which was used as a representative of the tricyclic compound (I), was increased up by mixing MCT into liquefied hydrofluoroalkanes. The addition of MCT enables the filling of FK506 as a solution into aerosol system. As a result, the change of spray performance will not be caused by aggregation of FK506 crystalline particles and the emitted dose uniformity of FK506 can be more reliable. The aerosol compositions used in this study were prepared according to a similar manner to that of Example 2.

TABLE 1

Effect of MCT Content on the Solubility of FK506 in HFAs

| MCT content | FK506 content (w/v %) in HFA-227 | | | | FK506 content (w/v %) in HFA-134a | |
|---|---|---|---|---|---|---|
| (%) | 0.05 | 0.1 | 0.2 | 0.5 | 0.05 | 0.2 |
| 0.05 | ○ | — | — | — | ○ | — |
| 0.5 | ○ | ○ | — | — | ○ | — |
| 2 | ○ | ○ | ○ | — | ○ | ○ |
| 5 | ○ | ○ | ○ | — | ○ | ○ |

○: solution
—: suspension

Moreover, since the medium-chain fatty acid triglyceride has an oily consistency at room temperature, it car be well 35 kneaded with the tricyclic compound (I) and after distributing the resulting kneaded mass into the dispensers, HFA can be filled thereinto under cooling or elevated pressure. The above achieved a remarkable uniformity of the content of the tricyclic compound (I) per dispenser.

Therefore, there is no variation in the delivery dose of the active ingredient on valve actuation.

The form of the aerosol composition of the present invention can be a solution-type or a suspension-type.

Therefore, depending on the amount of the content of the tricyclic compound (I) or its pharmaceutically acceptable salt thereof and/or MCT, the form of the aerosol composition of the present invention can be selective.

(2) Further, the addition of MCT was found to generate the novel characteristics in FK506 aerosol composition. For instance, the mass median aerodynamic diameter (MMAD) calculated from the aerodynamic particle size distribution as mentioned below, increased in proportion to MCT amount added (Table 2).

Aerodynamic Particle Size Distribution

According to the conventional method in USP23 (Apparatus 1), the aerodynamic particle size distribution was assessed from FK506 amount in each stage after applying one mg FK506 to multistage cascade impactor by firing FK506 aerosol composition. FK506 measurement was conducted by HPLC method and the MMAD was calculated from the particle size distribution. The FK506 aerosol compositions were prepared according to a similar manner to that of the below-mentioned Example 2.

TABLE 2

Effect of MCT Content on Aerodynamic Particle Size of 0.05% FK506 Aerosol Composition with HFAs.

| Propellant | MCT content (%) | Mass Median Aerodynamic Diameter (μm) |
|---|---|---|
| HFA-227 | 0.05 | 1.5 |
| | 0.5 | 1.7 |
| | 1 | 2.5 |
| | 2 | 3.1 |
| | 5 | 4.0 |
| HFA-134a | 0.5 | 1.6 |

(3) Moreover, FK506 release rate from the mist particles was studied according to the below-mentioned Dissolution Test. Thereby, it was confirmed that the release rate of FK506 was declined with addition of MCT as presented in Table 3. Especially, such a release rate was apt to be slower in solution than in suspension. These results clarified that FK506 release rate can be regulated by controlling the amount of MCT.

Dissolution Test

FK506 dissolution from the mist particles after firing FK506 aerosol composition was examined in distilled water at 37° C. using the paddle method at 50 rpm, according to the dissolution test method in JP12. The emitted dose from aerosol composition was adjusted to be one mg FK506 as a total in the test fluid. FK506 was measured by HPLC method. The FK506 aerosol compositions were prepared according to a similar manner to that of Example 2.

TABLE 3

Effect of MCT Content on Dissolution Rate of FK506

| Propellant | MCT content (%) | T 50% (min) FK506 0.05% | T 50% (min) FK506 0.2% |
|---|---|---|---|
| HFA-227 | 0 | 5 | 9 |
| | 0.5 | 30 | 12 |
| | 1 | 38 | 15 |
| | 2 | 43 | 28 |
| | 5 | 51 | 37 |

TABLE 3-continued Effect of MCT Content on Dissolution Rate of FK506

| Propellant | MCT content (%) | T 50% (min) | |
|---|---|---|---|
| | | FK506 0.05% | FK506 0.2% |
| HFA-134a | 0.5 | 29 | 11 |
| | 2 | 41 | 25 |

These novel characters suggested to enable to optimize the selectivity of pulmonary drug delivery and adjust drug absorption rate at delivered site, which means that the tricyclic compound (I) or a pharmaceutically acceptable salt thereof can be released sustainedly and that its toxicity can be reduced thereby.

Industrial Field of Utilization

The aerosol composition of the present invention is useful for the treatment and/or prevention of various diseases topically and/or systemically.

Especially, due to the pharmacological activities of the tricyclic compound (I), the aerosol composition comprising it of the present invention is useful for the treatment and/or prevention of reversible obstructive airways disease, which includes conditions such as asthma (e.g. bronchial asthma, allergic asthma, intrinsic asthma, extrinsic asthma and dust asthma), particularly chronic or inveterate asthma (e.g. late asthma and airway hyper-responsiveness), bronchitis and the like.

And further, the aerosol composition according to the present invention, due to the pharmacological activities, such as immunosuppressive activity and antimicrobial activity, of the tricyclic compound (I), is useful for the treatment and/or prevention of immune-mediated diseases such as rejection by transplantation of organs or tissues such as heart, kidney, liver, bone marrow, skin, cornea, lung, pancreas, small intestine, limb, muscle, nerve, intervertebral disk, trachea, etc.; graft-versus-host diseases by medulla ossium transplantation; autoimmune diseases such as rheumatoid arthritis, systemic lupus erythematosus, Hashimoto's thyroiditis, multiple sclerosis, myasthenia gravis, type I diabetes, and the like; and further infectious diseases caused by pathogenic microorganisms.

Further, the aerosol composition of the present invention is also useful for the treatment and the prophylaxis of inflammatory and hyperproliferative skin diseases and cutaneous manifestations of immunologically-mediated illnesses, such as psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitides, erythemas, cutaneous eosinophilias, lupus erythematosus, acne and alopecia areata;

various eye diseases such as autoimmune diseases and so on (e.g. keratoconjunctivitis, vernal conjunctivitis, uveitis associated with Behcet's disease, keratitis, herpetic keratitis, conical keratitis, dystrophia epithelialis corneae, corneal leukoma, ocular pemphigus, Mooren's ulcer, scleritis, Graves' ophthalmopathy, Vogt-Koyanagi-Harada syndrome, sarcoidosis, etc.);

inflammation of mucosa and blood vessels such as gastric ulcers, vascular injury caused by ischemic diseases and thrombosis, ischemic bowel disease, enteritis, necrotizing enterocolitis, intestinal lesions associated with thermal burns, leukotriene $B_4$-mediated diseases;

intestinal inflammations/allergies such as coeliac disease, proctitis, eosinophilic gastroenteritis, mastocytosis, Crohn's disease and ulcerative colitis;

food related allergic diseases which have symptomatic manifestation remote from the gastro-intestinal tract, for example, migraine, rhinitis and eczema;

renal diseases such as interstitial nephritis, Good-pasture's syndrome, hemolytic-uremic syndrome and diabetic nephropathy;

nervous diseases such as multiple myositis, Guillain-Barré syndrome, Ménière's disease and radiculopathy;

endocrine diseases such as hyperthyroidism and Basedow's disease;

hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia;

bone diseases such as osteoporosis;

respiratory diseases such as sarcoidosis, pulmonary fibrosis and idiopathic interstitial pneumonia; skin diseases such as dermatomyositis, leukoderma vulgaris, ichthyosis vulgaris, photoallergic sensitivity and cutaneous T cell lymphoma;

circulatory diseases such as arteroiosclerosis, atherosclerosis, aortitis syndrome, polyarteritis nodosa and myocardosis;

collagen diseases such as scleroderma, Wegener's granuloma and Sjögren's syndrome;

adiposis;

eosinophilic fasciitis;

periodontal disease such as lesion of gingiva, periodontium, alveolar bone, substantia ossea dentis;

nephrotic syndrome such as glomerulonephritis;

male pattern alopecia or alopecia senilis;

muscular dystrophy;

pyoderma and Sezary's syndrome;

Addison disease;

active oxygen-mediated diseases, for example, organ injury such as ischemia-reperfusion injury of organs (e.g. heart, liver, kidney, digestive tract) which occurs on preservation, transplantation or ischemic diseases (e.g. thrombosis, cardiac infarction): intestinal diseases such as endotoxin-shock, oseudomembranous colitis, colitis caused by drug or radiation: renal diseases such as ischemic acute renal insufficiency, chronic renal insufficiency: pulmonary diseases such as toxicosis caused by lung-oxygen or drug (e.g. paracort, bleomycins), lung cancer, pulmonary emphysema: ocular diseases such as cataracta, siderosis, retinitis, pigmentosa, senile macular degeneration, vitreous scarring, corneal alkali burn: dermatitis such as erythema multiforme, linear IgA bullous dermatitis, cement dermatitis: and others such as gingivitis, periodontitis, sepsis, pancreatitis, diseases caused by environmental pollution (e.g. air pollution), aging, carcinogens, metastasis of carcinoma, hypobaropathy;

diseases caused by histamine or leukotrience $C_4$ release;

and so on.

And further, the tricyclic compound (I) has liver regenerating activity and/or activities of stimulating hypertrophy and hyperplasia of hepatocytes. Therefore, the present aerosol composition is useful for the treatment and/or prevention of hepatic diseases such as immunogenic diseases (e.g. chronic autoimmune liver diseases such as the group consisting of autoimmune hepatic disease, primary biliary cirrhosis and sclerosing cholangitis), partial liver resection, acute liver necrosis (e.g. necrosis caused by toxins, viral hepatitis, shock or anoxia), hepatitis B, hepatitis non-A/non-B, cirrhosis and hepatic failure such as fulminant hepatitis late-onset hepatitis and "acute-on-chronic" liver failure (acute liver failure on chronic liver diseases).

And further, the present aerosol composition is useful for various diseases because of its useful pharmacological activity such as augmenting activity of chemotherapeutic effect, preventing or treating activity of cytomegalovirus infection, anti-inflammatory activity, and so on.

The aerosol composition of the present invention can also be obtained when the compounds disclosed in patent applications such as EP-A-353678, Japanese Patent Application No. 2(1990)-74330, PCT/GB90/01262, EP-A-413532, PCT/JP91/00314, British Patent Applications No. 9012963.6, No. 9014136.7, No. 9014681.2, No. 9014880.0, No. 9014881.8, No. 9015098.8, No. 9016115.9, and No. 9016693.5, EP-A-323865, EP-A-349061, EP-A-358508, EP-A-364031, EP-A-364032, EP-A-378317, EP-A-378320, EP-A-378321, EP-A-388153, EP-A-396399, EP-A-396400, EP-A-399579, EP-A-403242, EP-A-428365, EP-A-356399, GB 2225576 A, EP-A-402931, EP-A-427680, EP-A-445975, EP-A-455427, EP-A-463690, EP-A-464895, EP-A-466365, EP-A-478235, EP-A-480623, EP-A-509753, EP-A-515071, EP-A-520554, EP-A-526934, EP-A-530888, EP-A-532089, and EP-A-532088, W092/06992, WO92/20688, WO93/04679, WO93/05059, and WO93/04680, U.S. Pat. No. 5,149,701, German Patent Applications A-4021404, A-4028664, A-4028665, A-4028666, A-4028667, A-4028675, A-4028676, A-4028677, A-4028678, and A-4039587; and rapamycins such as rapamycin are employed instead of the tricyclic compound (I) or its pharmaceutically acceptable salt.

The present invention will be described hereinbelow with reference to the following Examples, but it is not intended to limit the scope of the invention.

EXAMPLE 1

FK506 was finely divided to a particle size of 2–3 μm by using a jet mill and the resulting powders were kneaded with Miglyol 812.

After distribution of the kneaded mass, each dispenser was filled with HFA-227 cooled to −20° C. beforehand and fitted with a valve to provide an aerosol product containing the following ingredients per unit (5 ml). (cold filling method)

| | |
|---|---|
| FK506 | 10 mg (0.2 (w/v)%) |
| Miglyol 812 | 25 mg (0.5 (w/v)%) |
| HFA-227 | 5 ml |

EXAMPLE 2

Dispensers were charged with the kneaded mass containing the following ingredients per unit (5 ml) which were obtained according to a similar manner to that of Example 1 and, after installation of the valve, each dispenser was filled with HFA-227 pressurized to 20 atms at room temperature to provide a medicinal aerosol composition of the same composition as that of Example 1. (Pressure filling method)

| | |
|---|---|
| FK506 | 5 mg (0.1 (w/v)%) |
| Miglyol 812 | 10 mg (0.2 (w/v)%) |
| HFA-227 | 5 ml |

EXAMPLES 3–11

The following aerosol compositions were provided in the same manner as Example 1 or Example 2.

| Examples | Tricyclic compound (Content (w/v%)) | Medium-chain fatty acid triglyceride (w/v%) | Propellant (5 ml) |
|---|---|---|---|
| 3 | FK506 (0.05) | Miglyol 812 (0.05) | HFA-227 |
| 4 | FK506 (0.1) | Miglyol 812 (0.5) | HFA-227 |
| 5 | FK506 (0.2) | Miglyol 812 (2) | HFA-227 |
| 6 | FK506 (0.5) | Miglyol 812 (5) | HFA-227 |
| 7 | FK506 (0.05) | Miglyol 812 (0.05) | HFA-134a |
| 8 | FK506 (0.2) | Miglyol 812 (5) | HFA-134a |
| 9 | FK506 (0.1) | Panacete 810 (0.2) | HFA-134a |
| 10 | FK506 (0.4) | Coconard (1) | HFA-134a |
| 11 | FR900520 (0.1) | Miglyol 812 (0.2) | HFA-227 |

EXAMPLE 12

The aerosol composition containing the following ingredients per unit (5 ml) was also prepared according to a similar manner to that of Example 2.

| | |
|---|---|
| FK506 | 10 mg |
| Miglyol 812 | 25 mg |
| Polyvinylpyrrolidone | 0.25 mg |
| HFA-227 | 5 ml |

What is claimed is:

1. An aerosol composition comprising a tricyclic compound (I) of the following formula:

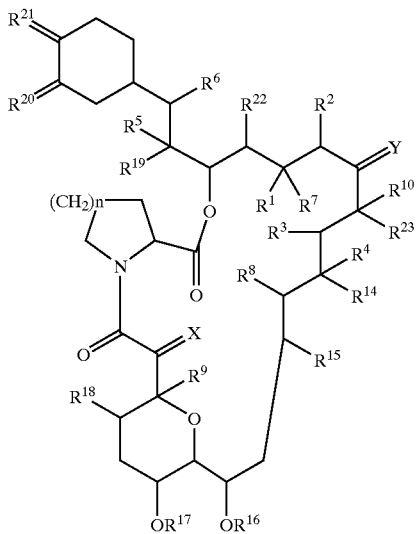

wherein each of adjacent pairs of $R^1$ and $R^2$, $R^3$ and $R^4$ or $R^5$ and $R^6$ is independently
(a) two adjacent hydrogen atoms, or
(b) may form another bond formed between the carbon atoms to which they are attached,
and further, $R^2$ may be an alkyl group;
$R^7$ is a hydrogen atom, a hydroxy group, a protected hydroxy group, or an alkoxy group or an oxo group together with $R^1$; each of $R^8$ and $R^9$ is independently a hydrogen atom or a hydroxy group;
$R^{10}$ is a hydrogen atom, an alkyl group, an alkyl group substituted by one or more hydroxy groups, an alkenyl group, an alkenyl group substituted by one or more hydroxy groups or an alkyl group substituted by an oxo group;
X is an oxo group, (a hydrogen atom and a hydroxy group), (a hydrogen atom and a hydrogen atom), or a group represented by the formula —CH$_2$O—;
Y is an oxo group, (a hydrogen atom and a hydroxy group), (a hydrogen atom and a hydrogen atom), or a group represented by the formula N—NR$^{11}$R$^{12}$ or N—OR$^{13}$;
each of $R^{11}$ and $R^{12}$ is independently a hydrogen atom, an alkyl group, an aryl group or a tosyl group;
each of $R^{13}$, $R^{14}$, $R^{15}$, $R^{16}$, $R^{17}$, $R^{18}$, $R^{19}$, $R^{22}$ and $R^{23}$ is independently a hydrogen atom or an alkyl group;
each of $R^{20}$ and $R^{21}$ is independently an oxo group, ($R^{20}$a and a hydrogen atom) or ($R^{21}$a and a hydrogen atom), in which each of $R^{20}$a and $R^{21}$a is independently a hydroxy group, an alkoxy group or a group represented by the formula —OCH$_2$OCH$_2$CH$_2$OCH$_3$, or $R^{21}$a is a protected hydroxy group, or $R^{20}$a and $R^{21}$a may together represent an oxygen atom in an epoxide ring;
n is an integer of 1 or 2; and
in addition to the above definitions, Y, $R^{10}$ and $R^{23}$ may represent a pyrrolyl ring or a tetrahydrofuryl ring optionally substituted by one or more groups selected from the group consisting of an alkyl, a hydroxy, an alkyl substituted by one or more hydroxy groups, an alkoxy, a benzyl and a group of the formula —CH$_2$Se(C$_6$H$_5$);
or a pharmaceutically acceptable salt thereof, a liquefied hydrofluoroalkane and a medium-chain fatty acid triglyceride.

2. The aerosol composition as claimed in claim 1, in which the tricyclic compound (I) or a pharmaceutically acceptable salt thereof is contained in amount of 0.001 to 10 w/v %.

3. The aerosol composition as claimed in claim 1, in which the tricyclic compound (I) is the one therein each of adjacent pairs of $R^3$ and $R^4$ or $R^5$ and $R^6$ independently may form another bond formed between the carbon atoms to which they are attached;
each of $R^8$ and $R^{23}$ is independently a hydrogen atom;
$R^9$ is a hydroxy group;
$R^{10}$ is a methyl group, an ethyl group, a propyl group or an allyl group;
X is (a hydrogen atom and a hydrogen atom) or an oxo group;
Y is an oxo group;
each of $R^{14}$, $R^{15}$, $R^{16}$, $R^{17}$, $R^{18}$, $R^{19}$ and $R^{22}$ is a methyl group;
each of $R^{20}$ and $R^{21}$ is independently ($R^{20}$a and a hydrogen atom) or ($R^{21}$a and a hydrogen atom) in which each of $R^{20}$a and $R^{21}$a is a hydroxy group or an alkoxy group, or $R^{21}$a is a protected hydroxy group; and
n is an integer of 1 or 2.

4. The aerosol composition as claimed in claim 3, in which the tricyclic compound (I) is the one wherein $R^7$ is a hydrogen atom, a hydroxy group or a protected hydroxy group; X is an oxo group; $R^{20}$a is a methoxy group; $R^{21}$a is a hydroxy group or a protected hydroxy group.

5. The aerosol composition as claimed in claim 4, in which the tricyclic compound (I) is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

6. The aerosol composition as claimed in claim 1, in which the liquefied hydrofluoroalkane is 1,1,1,2-tetrafluoroethane.

7. The aerosol composition as claimed in claim 1, in which the medium-chain fatty acid triglyceride is CH$_3$(CH$_2$)$_n$COOH, wherein n is 4–10.

8. The aerosol composition as claimed in claim 1, which further comprises an optional additive selected from the group consisting of polyvinylpyrrolidone and ethanol.

9. A process for a preparation of the aerosol composition as claimed in claim 1, comprising;
(1) kneading said tricyclic compound (I) or a pharmaceutically acceptable salt thereof with a medium-chain fatty acid triglyceride,
(2) distributing the resulting kneaded mass into dispensers, and
(3) filling each dispenser with said liquefied hydrofluoroalkane under cooling or elevated pressure.

10. The aerosol composition as claimed in claim 1, in which the liquefied hydrofluoroalkane is 1,1,1,2,3,3,3-heptafluoropropane.

11. The aerosol composition as claimed in claim 1, in which said medium-chain fatty acid triglyceride is present in an amount range of from 0.05 to 5 w/v %.

12. The aerosol composition as claimed in claim 1, in which said medium-chain fatty acid triglyceride is present in an amount range of from 0.1 to 2 w/v %.

13. The process as claimed in claim 9, wherein said medium-chain fatty acid triglyceride is CH$_3$(CH$_2$)$_n$COOH, wherein n is 4–10.

* * * * *

UNITED STATES PATENT AND TRADEMARK OFFICE
CERTIFICATE OF CORRECTION

PATENT NO.   : 6,524,556 B2
DATED        : February 17, 2005
INVENTOR(S)  : Murata et al.

It is certified that error appears in the above-identified patent and that said Letters Patent is hereby corrected as shown below:

Column 14,
Lines 38-41, should read
7. The aerosol composition as claimed in claim 1, in which the medium-chain fatty acid triglyceride is --a triglyceride of saturated fattyl acids of the formula-- CH#(CH@)nCOOH, wherein n is 4-10.
Lines 64-65, should read
13. The process as claimed in claim 9, wherein said medium-chain fatty acid triglyceride is-- a triglyceride of saturated fatty acids of the formula-- CH3(CH2)nCOOH, wherein n is 4-10.

Signed and Sealed this

Nineteenth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,524,556 B2
DATED : February 17, 2005
INVENTOR(S) : Murata et al.

It is certified that error appears in the above-identified patent and that said Letters Patent is hereby corrected as shown below:

<u>Column 14,</u>
Lines 38-41, should read
7. The aerosol composition as claimed in claim 1, in which the medium-chain fatty acid triglyceride is -- a triglyceride of saturated fatty acids of the formula -- $CH_3(CH_2)_nCOOH$, wherein n is 4-10.
Lines 64-65, should read
13. The process as claimed in claim 9, wherein said medium-chain fatty acid triglyceride is-- a triglyceride of saturated fatty acids of the formula -- $CH_3(CH_2)_nCOOH$, wherein n is 4-10.

This certificate supersedes Certificate of Correction issued April 19, 2005.

Signed and Sealed this

Fifth Day of July, 2005

JON W. DUDAS
*Director of the United States Patent and Trademark Office*